United States Patent [19]
Hodges et al.

[11] Patent Number: 5,980,709
[45] Date of Patent: Nov. 9, 1999

[54] METHOD OF DEFINING AN ELECTRODE AREA

[75] Inventors: Alastair McIndoe Hodges; Oddvar Johansen, both of Victoria; Thomas William Beck, Windsor, all of Australia

[73] Assignee: USF Filtration and Separations Group, Timonium, Md.

[21] Appl. No.: 08/973,086

[22] PCT Filed: Apr. 11, 1996

[86] PCT No.: PCT/AU96/00210

§ 371 Date: Oct. 10, 1997

§ 102(e) Date: Oct. 10, 1997

[87] PCT Pub. No.: WO96/32635

PCT Pub. Date: Oct. 17, 1996

[30] Foreign Application Priority Data

Apr. 12, 1995 [AU] Australia .................. PN2393

[51] Int. Cl.$^6$ .............. G01N 27/26; C25B 11/00
[52] U.S. Cl. .......... 204/409; 427/2.11; 210/348; 204/286; 204/403
[58] Field of Search ............... 427/2.11, 2.12, 427/2.13; 210/348; 204/403, 280, 286, 409, 415

[56] References Cited

U.S. PATENT DOCUMENTS

| | | | |
|---|---|---|---|
| 4,224,125 | 9/1980 | Nakamura et al. | 204/195 B |
| 4,233,029 | 11/1980 | Columbus | 23/230 R |
| 4,254,083 | 3/1981 | Columbus | 422/55 |
| 4,259,165 | 3/1981 | Miyake | 204/415 |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,307,188 | 12/1981 | White | 435/4 |
| 4,374,013 | 2/1983 | Enfors | 204/195 |
| 4,404,066 | 9/1983 | Johnson | 204/1 |
| 4,431,004 | 2/1984 | Bessman et al. | 128/635 |
| 4,517,287 | 5/1985 | Scheibe et al. | 435/4 |
| 4,517,291 | 5/1985 | Seago | 435/14 |

(List continued on next page.)

FOREIGN PATENT DOCUMENTS

| | | |
|---|---|---|
| 54873/94 | 2/1993 | Australia . |
| 31042/93 | 7/1993 | Australia . |
| 0 251 915 A2 | 1/1988 | European Pat. Off. . |
| 0 255 291 A1 | 2/1988 | European Pat. Off. . |
| 0 266 204 A2 | 4/1988 | European Pat. Off. . |
| 0 278 647 A2 | 8/1988 | European Pat. Off. . |
| 0 299 779 A2 | 1/1989 | European Pat. Off. . |
| 0 351 516 A2 | 1/1990 | European Pat. Off. . |
| 0 351 892 A2 | 1/1990 | European Pat. Off. . |
| 0 171 375 A1 | 5/1990 | European Pat. Off. . |

(List continued on next page.)

OTHER PUBLICATIONS

Derwent Abstract Accession No. 92 119462/15, Class S03, JP,A, 04–62463.(Tokyo Yogyo K.K.) Feb. 27, 1992.

*Primary Examiner*—T. Tung
*Assistant Examiner*—Alex Noguerola
*Attorney, Agent, or Firm*—Knobbe, Martens, Olson & Bear, LLP

[57] ABSTRACT

The present invention relates to a method for defining an area (4) of a layer on a porous substrate comprising compressing a volume of the substrate to produce a compressed region (8) which defines, or which in combination with an edge (7) of the substrate or of the layer defines, a boundary of the area and which substantially prevents the transport of material through or across its surface. The present invention also relates to an electrochemical sensing device comprising: a porous substrate; and an electrode (1) on one side of the substrate; wherein a region of the substrate is compressed to an extent which forms a barrier to migration of electrolyte within the substrate, the compressedregion defining, or in combination with an edge of the substrate or the electrode defining, a zone on the electrode of predetermined area.

40 Claims, 5 Drawing Sheets

U.S. PATENT DOCUMENTS

| | | | |
|---|---|---|---|
| 4,533,440 | 8/1985 | Kim | 204/1 |
| 4,545,382 | 10/1985 | Higgins et al. | 128/635 |
| 4,552,840 | 11/1985 | Riffer | 205/778 |
| 4,629,563 | 12/1986 | Wrasidlo | 210/500.34 |
| 4,654,197 | 3/1987 | Lilja et al. | 422/56 |
| 4,664,119 | 5/1987 | Bessman et al. | 204/415 |
| 4,711,245 | 12/1987 | Higgins et al. | 128/635 |
| 4,774,039 | 9/1988 | Wrasidlo | 264/41 |
| 4,790,925 | 12/1988 | Miller et al. | 204/415 |
| 4,900,424 | 2/1990 | Birth et al. | 204/409 |
| 4,919,770 | 4/1990 | Preidel et al. | 204/153.1 |
| 4,963,815 | 10/1990 | Hafeman | 205/777.5 |
| 5,059,908 | 10/1991 | Mina | 324/444 |
| 5,064,516 | 11/1991 | Rupich | 204/415 |
| 5,120,420 | 6/1992 | Nankai et al. | 204/403 |
| 5,122,244 | 6/1992 | Hoenes et al. | 204/153.1 |
| 5,126,034 | 6/1992 | Carter et al. | 204/403 |
| 5,128,015 | 7/1992 | Szuminsky et al. | 204/403 |
| 5,141,868 | 8/1992 | Shanks et al. | 435/288 |
| 5,151,166 | 9/1992 | Harral et al. | 204/425 |
| 5,192,415 | 3/1993 | Yoshioka et al. | 204/403 |
| 5,229,282 | 7/1993 | Yoshioka et al. | 435/177 |
| 5,272,087 | 12/1993 | El Murr et al. | 435/291 |
| 5,320,732 | 6/1994 | Nankai et al. | 204/403 |
| 5,382,346 | 1/1995 | Uenoyama et al. | 204/403 |
| 5,384,028 | 1/1995 | Ito | 204/403 |
| 5,385,846 | 1/1995 | Kuhn et al. | 436/70 |
| 5,393,399 | 2/1995 | Van Den Berg et al. | 204/412 |
| 5,413,690 | 5/1995 | Kost et al. | 204/403 |
| 5,437,999 | 8/1995 | Diebold et al. | 435/288 |
| 5,508,171 | 4/1996 | Walling et al. | 205/777.5 |
| 5,509,410 | 4/1996 | Hill et al. | 128/637 |
| 5,527,446 | 6/1996 | Kosek et al. | 204/415 |
| 5,567,302 | 10/1996 | Song et al. | 205/777.5 |
| 5,611,908 | 3/1997 | Mattiessen et al. | 205/775 |
| 5,620,579 | 4/1997 | Genshaw et al. | 204/402 |
| 5,628,890 | 5/1997 | Carter et al. | 204/403 |
| 5,645,709 | 7/1997 | Birch et al. | 205/775 |

FOREIGN PATENT DOCUMENTS

| | | |
|---|---|---|
| 0 400 918 A1 | 12/1990 | European Pat. Off. . |
| 0 418 404 A1 | 3/1991 | European Pat. Off. . |
| 0 451 981 A2 | 10/1991 | European Pat. Off. . |
| 0 560 336 A1 | 9/1993 | European Pat. Off. . |
| 31 03 464 A1 | 8/1982 | Germany . |
| 3103-464 | 8/1982 | Germany . |
| 62-22874 | 10/1987 | Japan . |
| 3-167464 (A) | 7/1991 | Japan . |
| 4-66112 (A) | 3/1992 | Japan . |
| 1351-627 | 11/1987 | U.S.S.R. . |
| 2 020 424 | 11/1979 | United Kingdom . |
| 2 154 735 | 9/1985 | United Kingdom . |
| 2 201 248 | 8/1988 | United Kingdom . |
| 2 235 050 | 2/1991 | United Kingdom . |
| WO 89/08713 | 9/1989 | WIPO . |
| WO 92/15701 | 9/1992 | WIPO . |
| WO 94/02842 | 2/1994 | WIPO . |
| WO 95/16198 | 6/1995 | WIPO . |
| WO 97/00441 | 1/1997 | WIPO . |

METHOD OF DEFINING AN ELECTRODE AREA

TECHNICAL FIELD

The present invention relates to a method for defining an area of a coating or layer attached to or in contact with a porous substrate. More particularly, the present invention relates to a method wherein the coating or layer is an electrode. Although the invention will be described with reference to its application in the electrochemical area it is not intended that the invention be limited to that use. It may extend to any application where a defined area of a porous substrate is required.

BACKGROUND ART

In the past it has been found that whenever quantitative electrochemical measurements are performed it is necessary to have both a reproducible and accurately defined electrode area which is in contact with the sample being analysed. When performing a measurement in a bulk solution the usual practice has been either to have the electrode immersed to a certain level in the liquid or alternatively to have an insulation layer applied to the electrode to leave only a precisely defined area in contact with the solution. These practices have proved to be relatively expensive and unreliable. It has also been found that when these methods are used it is difficult to prevent leakage and contact with the electrode outside the defined area, especially when the substrate upon which the electrode is placed is porous.

The present invention seeks to overcome or at least ameliorate the problems of the prior art by providing a method which is inexpensive, simple to apply and reliable.

SUMMARY OF THE INVENTION

According to one aspect the present invention consists in a method for defining an area of a layer on a porous substrate comprising compressing a volume of the substrate to produce a compressed region which defines, or which in combination with an edge of the substrate or of the layer defines, a boundary of the area and which substantially prevents the transport of material through or across its surface.

According to a second aspect the invention consists in an electrochemical sensing device comprising:
 a porous substrate; and
 an electrode on one side of the substrate; wherein a region of the substrate is compressed to an extent which forms a barrier to migration of electrolyte within the substrate, the compressed region defining, or in combination with an edge of the substrate or the electrode defining, a zone on the electrode of predetermined area.

According to a third aspect the porous substrate of the second aspect is a membrane that is permeable to a fluid containing a first species to be analysed but substantially impermeable to a second species contained in the fluid, the second species being of a kind which would interfere with electrochemical sensing of the first species.

Preferably, the layer, which may be attached to or in contact with the porous substrate or may be a coating applied to the substrate, is an electrode and the area being defined is an electrode area. When the layer is an electrode it is usually sputter deposited on the surface of the substrate so as to form a continuous film on the surface. However, other methods such as electroless plating, electroplating, evaporation, anodization or the like can be used to form the electrode. Usually the film thickness on the substrate is 10–200 nm, more preferably 60–120 nm.

Materials which would be suitable as an electrode include gold, silver, platinum, palladium, iridium, lead, and alloys of those metals, carbon, carbon mixed with a binding material, and silver partially covered with a porous layer of an insoluble silver salt such as silver chloride, silver bromide, silver iodide, silver ferricyanide and silver ferrocyanide. In electrochemical sensing devices according to the invention there will typically be two or more electrodes and these may be disposed on one side of the substrate or on opposite sides of the substrate.

In a preferred form the resulting substrate produced from the method of the invention will have at least two discrete regions—one region being compressed and the other region being uncompressed. This resulting substrate has been found to be particularly useful when used as an electrochemical sensing device. When a sample is placed on the uncompressed region of the resulting substrate, migration of the sample to another region of that substrate, being divided from the first region by the compressed region, is substantially prevented. It has been found that the sample is confined to a predetermined area of the resulting substrate and therefore to a predetermined area of the electrode attached to or otherwise in contact with the resulting substrate.

The method of the present invention works by substantially eliminating or sufficiently constricting the porous structure of the substrate in the compressed region to render that region effectively impermeable.

The method of the present invention can be used alone or preferably, in conjunction with a blocker. A blocker, in the present invention, is a substance which is placed in the substrate such that it does not prevent the transport of material in the uncompressed regions of the substrate but assists in preventing transport of material in the compressed areas. Examples of material suitable as a blocker may include glucose, agar, gelatine, starch or the like.

In a preferred form the blocker is conveniently loaded into the precompressed porous substrate using the steps of:
 (a) dissolving the blocker in a suitable solvent;
 (b) wetting the substrate with the solution of the blocker; and then
 (c) removing the solvent by evaporation.

In another preferred form the porous substrate is of a kind having pores which increase in diameter from a smooth or shiny side to a rough side. The porous substrate is desirably of the kind disclosed in U.S. Pat. Nos. 4,629,563 and 4,774,039 both of which are incorporated herein in their entirety by reference. However according to end use the substrate may be an asymmetric or symmetric membrane.

The substrate may be any suitable porous material that is compressible and which will maintain its mechanical integrity during compression. Examples of such materials include polymers or mixtures of polymers such as polysulfones, polyvinylidene halides such as polyvinylidene difluorides, tetrafluoroethene, polyamides, polyimides, polyethylenes, polypropylenes, polyacrylonitrites, polycarbonates or the like. The materials may be in the form of a sheet, tube or hollow fibre which have microscopic or macroscopic pores.

The thickness of the substrate is selected with the end use in mind. Usually it is desirable for the substrate to be thin to minimise sample volume. However, sufficient thickness is required to provide mechanical strength for handling and to maintain sufficient separation between electrodes on opposite faces of the substrate to prevent electrical short circuits.

In some applications for example anodic stripping, larger sample volumes and greater thickness will be preferred. Preferred embodiments and illustrative examples of the present invention will now be described, by way of example only, with reference to the accompanying figures, in which:

BRIEF DESCRIPTION OF THE FIGURES

FIG. 1 illustrates a microporous substrate 10 in an uncompressed form having an electrode 1 being attached to or in contact with substrate 10. The thickness of the compressed substrate is preferably about 180 $\mu$m, more preferably from 30–150 $\mu$m. The pore size ranges from 10 kilodaltons cut-off (lower limit) to 5 microns and preferably from 0.1 $\mu$m to 0.8 $\mu$m, more preferably from 0.2 $\mu$m to 0.5 $\mu$m. Also shown in FIG. 1 is the magnified image which shows the uncompressed pores 2 of the substrate. When pressure is applied to an area 5 of the microporous substrate 10, one or more discrete compressed regions 8 are produced. Area 5 is an area on the surface of the microporous substrate to which pressure is applied to form compressed region 8, which lies below compression area 5. As shown in FIG. 2 and 3 the compressed regions 8 in combination with the edges 7 of the uncompressed region define a boundary of the area 4. This compressed region 8 substantially prevents the transport of material (not shown) through or across its volume.

Figure 1:
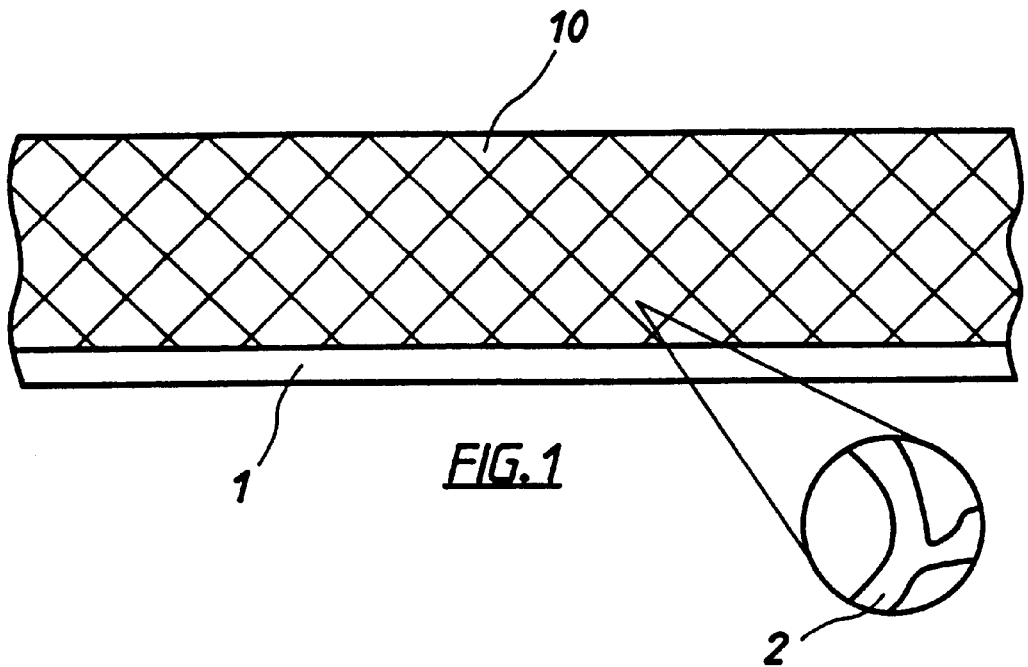
FIG. 1 shows a cross-sectional view of a microporous substrate in uncompressed form, with a portion shown as an enlarged image.
Figure 2:
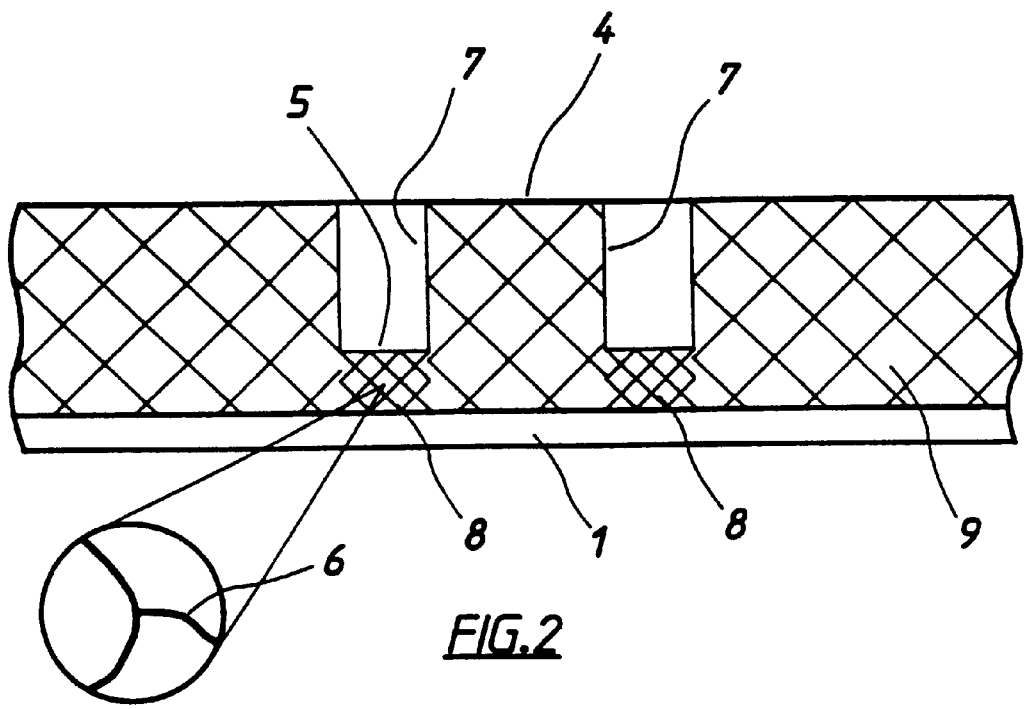
FIG. 2 shows the substrate of FIG. 1 with compressed regions in combination with the edge of the microporous substrate to define a perimeter of the area with a portion of the compressed region shown as an enlarged image.
Figure 3:
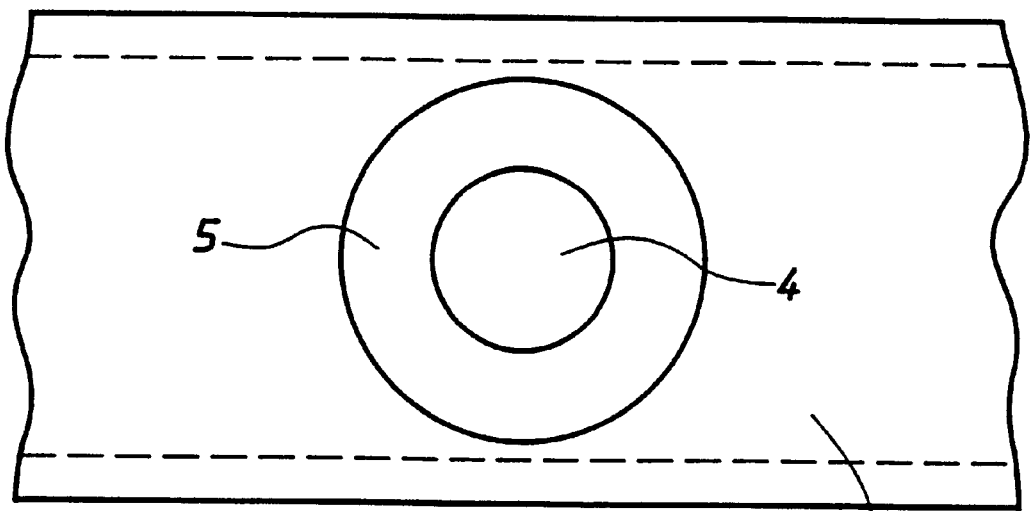
FIG. 3 shows a top view of the substrate of FIG. 2.
Figure 4:
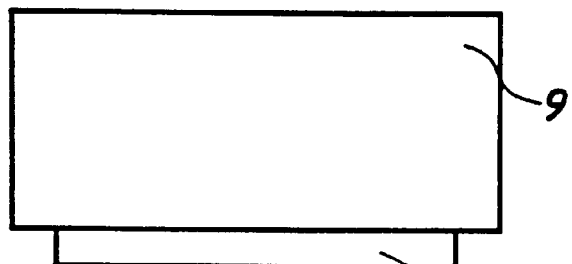
FIG. 4 shows an end view of the substrate of FIGS. 1 or 2.

The magnified image of FIG. 2 shows the pores 6 of region 8 which have been compressed so as to substantially prevent transportation of material across or through region 8.

Figure 5:
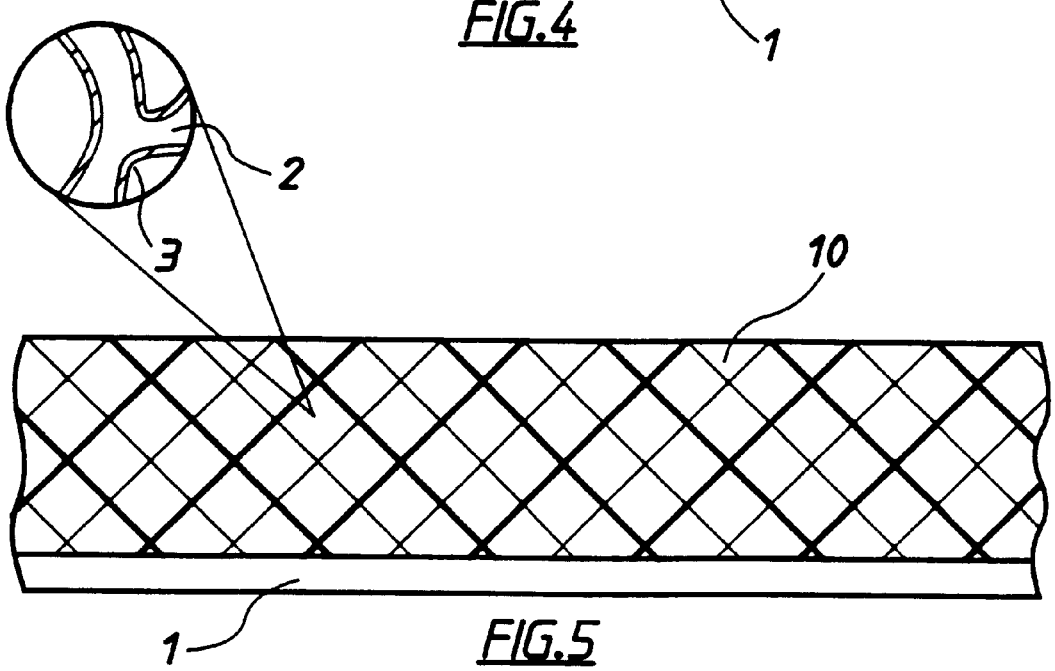
FIG. 5 is similar view to FIG. 1 where a blocker has been added to the substrate.
Figure 6:
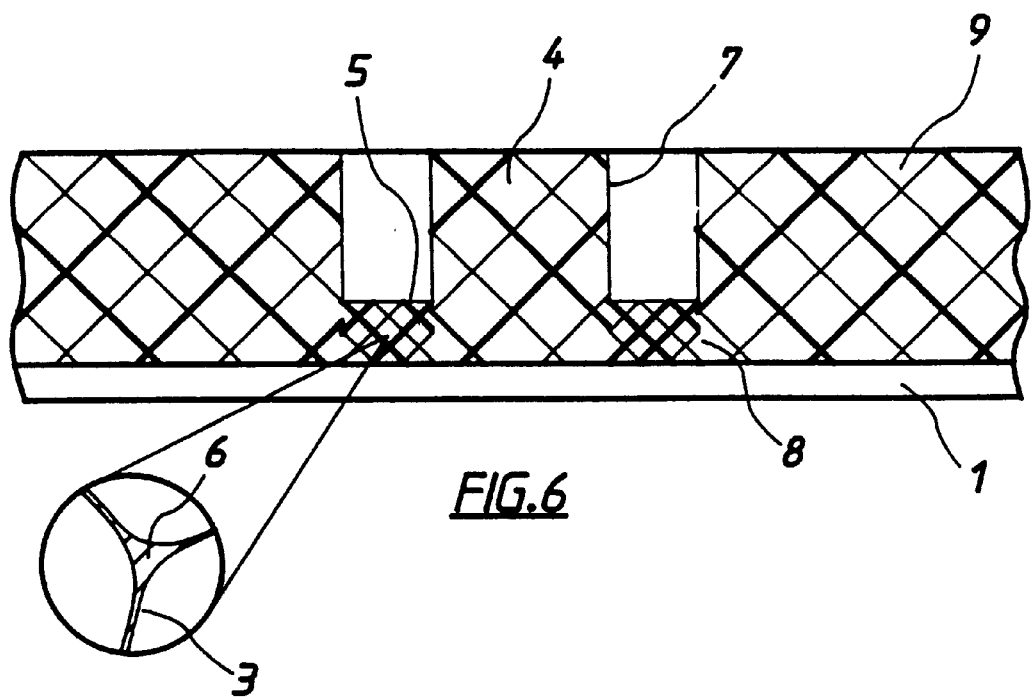
FIG. 6 is a similar view to FIG. 2 where a blocker has been added to the substrate.

FIGS. 5 and 6 illustrate the effect of the addition of a blocker 3. As shown in the magnified image of FIG. 6 the addition of blocker 3 makes the blockage of the pores 6 in region 8 more complete so as to prevent the transportation of material across or through it.

Figure 7:
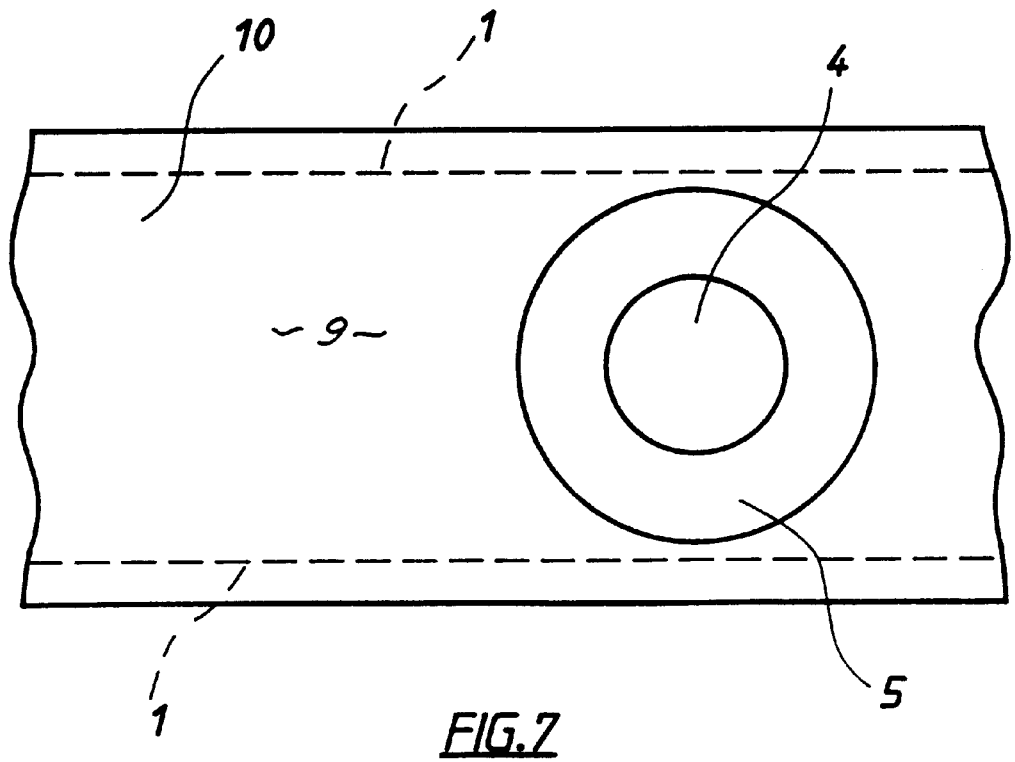
FIG. 7 is a top view of one embodiment differing in respect of defined target areas.
Figure 8:
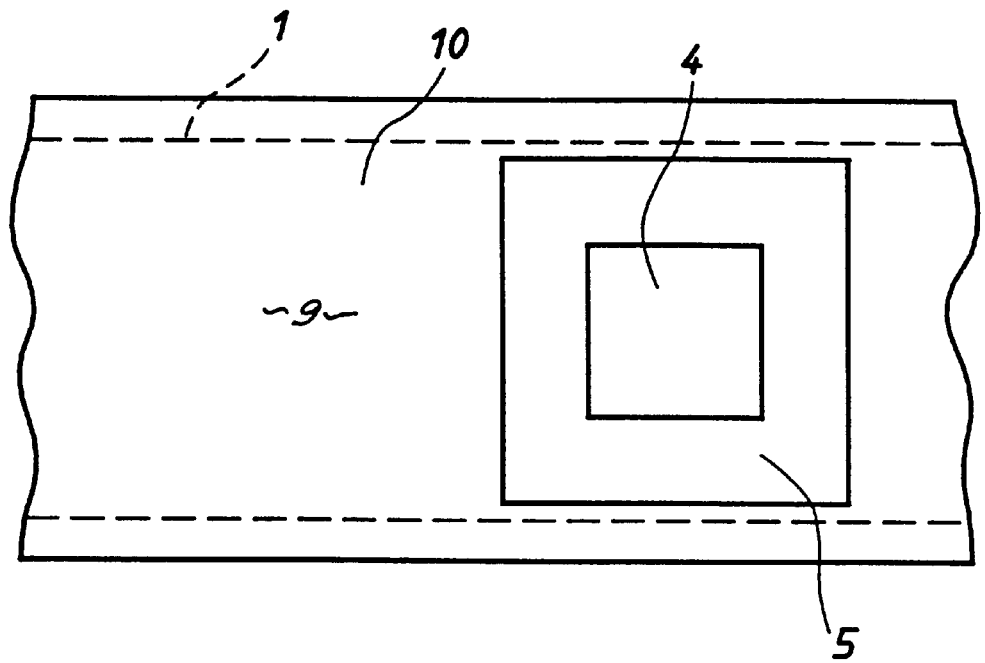
FIG. 8 is a top view of a second embodiment differing in respect of target areas.

FIGS. 7 and 8 illustrates the compressed area 5 being in the shape of a ring or square on one side of substrate 10 and overlying an electrode 1 on the opposite side. The compressed region 8 defines a boundary of an area 4 of the electrode and which substantially prevents the transport of material (not shown) through or across region 8 to adjoining regions 9.

Although not illustrated in the drawings the area 4 of electrode 1 may be defined partly by compressed region 8 or area 5 and partly by an electrode edge.

Figure 9:
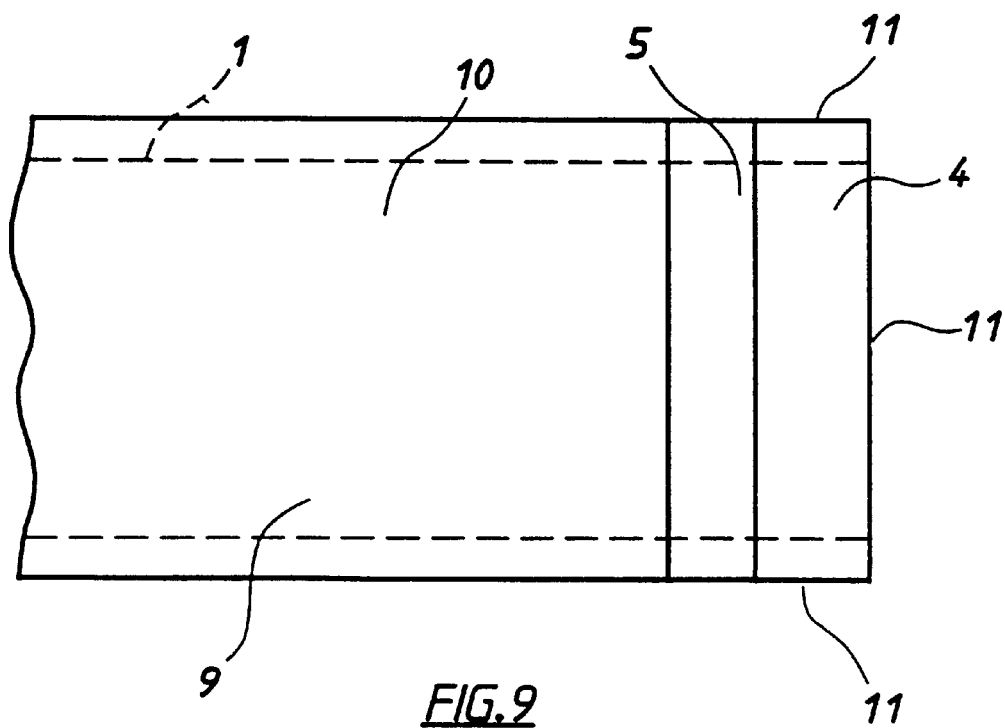
FIG. 9 is a top view of a third embodiment differing in respect of target areas.

FIG. 9 shows a rectangular area 4 being defined on one edge by compression area 5 and on the other edges by the edge 11 of uncompressed substrate 9.

Figure 10:
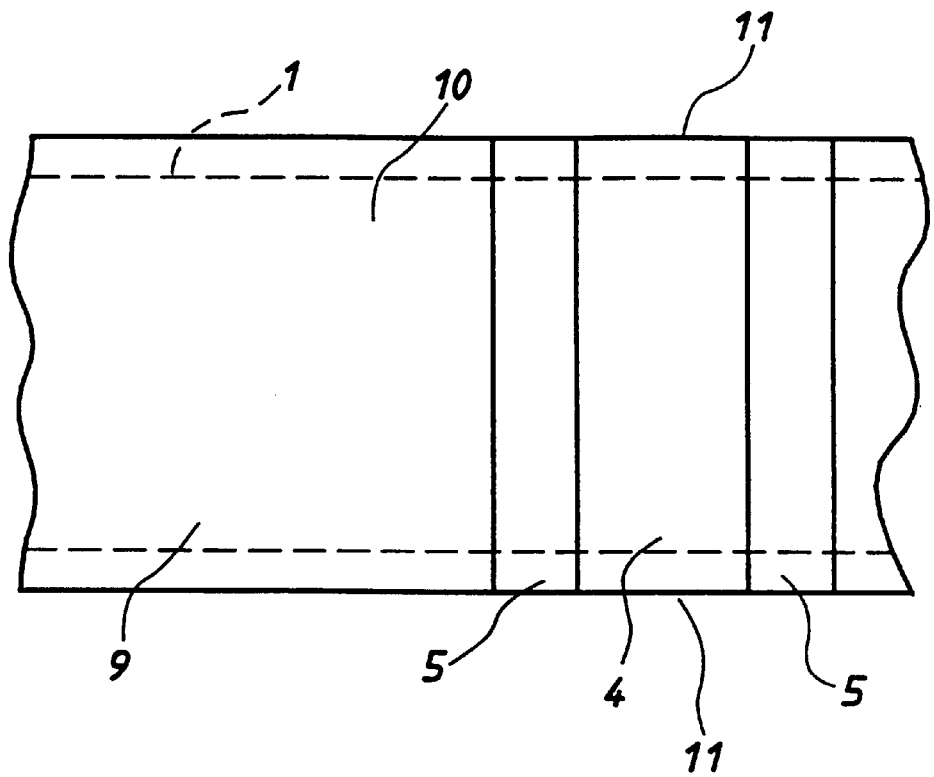
FIG. 10 is a top view of a fourth embodiment differing in respect of target areas.

FIG. 10 shows a rectangular area 4 being defined by two compression areas 5 in combination with two edges 11 of uncompressed substrate 9.

In the present invention the porous substrate is preferably pressed by means of a press or any suitable compressing process which will allow for at least one region of the porous substrate to be compressed. The amount of pressure to be applied varies between substrates, at both the high and low end of the pressure range. It is preferred that a sufficient amount of pressure is applied to the substrate which will collapse the pore structure of the substrate to achieve substantial non-porosity, but not too high so as to significantly destroy the mechanical integrity of the substrate.

An exemplification of the range of pressures needed to compress the porous substrate will now be described, with reference to the following examples and comparative examples.

BEST MODE OF CARRYING OUT THE INVENTION

EXAMPLE 1

A sheet of polysulfone substrate 150 $\mu$m thick with pores of between 0.2 $\mu$m and 0.5 $\mu$m was dipped into a solution which was 1 wt % gelatine in water. The excess liquid was wiped from the outside of the substrate and the substrate dried in an oven to remove the water. The substrate was then pressed with a pressure of 100 MPa such that a compressed area in the form of a ring was formed on the substrate. The ring had an internal diameter 8 mm and an external diameter of 10 mm.

10 $\mu$l of a solution of a dye (Rose Bengal) in water was dropped onto the substrate inside the ring. The dye solution was seen to spread to the inside edge of the compressed ring and then stop. No dye was visible outside the circular region defined by the compressed ring after approximately 1 hour, by which time the water in the dye solution had evaporated.

Comparative Example 1

As in example 1 except the substrate was pressed with a pressure of 30 MPa. At this pressure there was some leakage of the dye to outside the defined area.

EXAMPLE 2

As in example 1 except that the substrate was coated with approximately 60 nm of platinum which was used as an electrode. Also, instead of a dye solution being dropped onto the substrate a solution containing ferrocyanide and ferricyanide was used, a potential applied to the platinum electrodes and the current recorded over time. After an initial higher current the current stayed constant for approximately 10 minutes, after which time the substrate started to dry out and lose electrical connection. This constant current indicated that no spreading of the solution outside the defined area had occurred.

Comparative Example 2

As in example 1 except the substrate was pressed with a pressure of 55 MPa. Five defined areas were prepared. One showed some leakage of the dye outside the defined area, the other four showed no leakage.

EXAMPLE 3

As in example 2 except that a polyvinylidene difluoride substrate with approximately 0.2 $\mu$m pores was used.

EXAMPLE 4

As in example 1 except the substrate was pressed with a pressure of 80 MPa. At this pressure there was no leakage of the dye outside the defined area.

Comparative Example 4

As in example 1 except the substrate was not dipped into a gelatine solution. The pressure applied was 70 MPa. Four defined areas were prepared and the dye leaked to outside the defined area in all cases.

Comparative Example 5

As in example 1 except the substrate was not dipped into a gelatine solution and pressed with a pressure of 80 MPa. Five defined areas were prepared and the dye leaked to outside the defined area in four cases and no leakage was apparent in one case.

Comparative Example 6

As in example 1 except the substrate was not dipped into a gelatine solution and pressed with a pressure of 100 MPa. Three defined areas were prepared and the dye leaked to outside the defined area in one case and no leakage was apparent in two cases.

Preferably, the membrane in the present invention is permeable to a fluid containing a first species to be analysed but substantially impermeable to a second species. An exemplification of this preferred embodiment of the invention will now be described with reference to the following example.

Example A

A sheet of polysulfone 100 µm thick with pores of 0.2 µm was coated on one side with two 1 mm strips of platinum. A defined electrode area was prepared in accordance with the method of Example 1. A sample of blood to be analysed was brought into contact with the substrate on the opposite side on which the sensing electrode was coated and within the defined area. It was found that the membrane was impermeable to the interfering species erythrocytes (II) in the blood but permeable to glucose or cholesterol (I). The first species either glucose or cholesterol, could be analysed without interference from erythrocytes (II).

It will be understood that in an electrochemical sensing device it is usual to employ two or three electrodes and in that case all the electrodes may extend into or pass through an area defined by a barrier or barriers according to the invention. For example, the compressed barrier may define a square through which two strip electrodes pass. An area is thus defined on each electrode by the edges of that electrode and by the compressed barrier where the strip enters and leaves the square.

Example B

Figure 11:
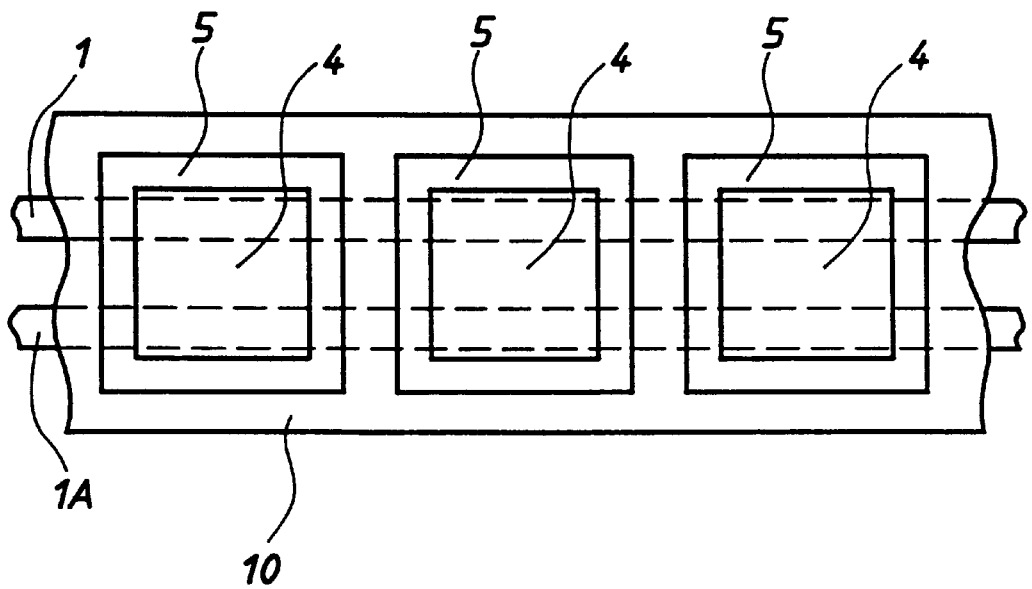
FIG. 11 shows a top view of a preferred embodiment of the invention.

In a highly preferred embodiment of the invention illustrated in FIG. 11, substrate 10 is in the form of a strip having electrodes 1, 1A on opposite sides of the strip. Both electrodes 1, 1A extend longitudinally of the strip which has a plurality of defined square areas 4 spaced apart along the strip length, each area being defined by a area 5, to which area compression pressure is applied in accordance with the invention.

Each area 4 defines a predetermined area of electrodes 1 and 1A (shown crosshatched). In use a sample may be placed on an area 4 nearest the strip end.

Measurements may be made by connecting suitable apparatus with the electrodes at the opposite strip end in a manner that is conventional. Thereafter the "used" area may be cut from the strip and the next area 4 now closest to the strip end may be used for the next sample.

If desired, an absorbent strip may be provided on the side remote from the sensor electrode to increase the sample volume and hence the signal or to reduce measuring times. Likewise if desired, one or more analytes might be contained within the volume of substrate bounded by compression area 5.

Although the invention has been described with reference to specific examples and Figures, it will be appreciated by those skilled in the art that the invention may be embodied in many other forms.

We claim:

1. A method for defining an area of a layer on a porous substrate comprising compressing a volume of the substrate to produce a compressed region which defines, or which in combination with an edge of the substrate or of the layer defines, a boundary of the area and which substantially prevents the transport of material through or across its surface.

2. A method according to claim 1, wherein the layer is either attached to or in contact with the porous substrate or is a coating applied to the substrate.

3. A method according to claim 1, wherein the layer is an electrode and the area being defined is an electrode area.

4. A method according to claim 3, wherein the electrode is formed on the surface of the substrate by a method selected from the group consisting of electroless plating, electroplating,, evaporation, and sputtering.

5. A method according to claim 4, wherein the electrode is sputter deposited on the surface of the substrate to form a continuous film.

6. A method according to claim 5, wherein the film thickness on the substrate is 10 to 200 nm.

7. A method according to claim 6, wherein the film thickness is 60 to 120 nm.

8. A method according to claim 3, wherein the electrode is made of materials selected from the group consisting of gold, silver, platinum, palladium, iridium, lead and alloys of those metals, carbon, carbon mixed with a binding material, and silver partially covered with a porous layer of an insoluble silver salt.

9. A method according to claim 8, wherein the insoluble silver salt is silver chloride, silver bromide, silver iodide, silver ferrocyanide or silver ferricyanide.

10. A method according to claims 1, further including a blocker in the substrate which assists in preventing transport of material in the compressed region.

11. A method according to claim 10, wherein the blocker is glucose, agar, gelatine or starch.

12. A method according to claim 10, wherein the blocker is loaded into the precompressed porous substrate using the steps of:

a) dissolving the blocker in a suitable solvent;

b) wetting the substrate with the solution of the blocker; and then c) removing the solvent by evaporation.

13. A method according to claim 1, wherein the substrate is made of a porous material selected from the group consisting of polymers or mixtures of polymers.

14. A method according to claim 13, wherein the polymers or mixtures of polymers consist of polysulfones, polyvinylidene halides, tetrafluoroethene, polyamides, polyimide, polyethylene, polypropylenes, polyacrylonitrides or polycarbonates.

15. A method according to claim 14, wherein the polyvinylidene halides are polyvinylidene difluorides.

16. A method according to claim 1, wherein the thickness of the compressed substrate is about 180 μm or less.

17. A method according to claim 16, wherein the thickness of the compressed substrate is from 30 μm to 150 μm.

18. A method according to any one of claims 1 to 17, wherein the pore size of the substrate ranges from 10 kilodaltons cut-off (lower limit) to 5 microns.

19. A method according to claim 18, wherein the pore size of the substrate ranges from 0.1 μm to 0.8 μm.

20. A method according to claim 19, wherein the pore size of the substrate ranges from 0.2 μm to 0.5 μm.

21. An electrochemical sensing device comprising:

a porous substrate; and an electrode on one side of the substrate; wherein a region of the substrate is compressed to an extent which forms a barrier to migration of electrolyte within the substrate, the compressed region defining, or in combination with an edge of the substrate or the electrode defining, a zone on the electrode of predetermined area.

22. An electrochemical sensing device according to claim 21, wherein the electrode is formed on one side of the substrate by a method selected from the group consisting of electroless plating, electroplating, evaporation, and sputtering.

23. An electrochemical sensing device according to claim 22, wherein the electrode is sputter deposited on the surface of the substrate to form a continuous film.

24. An electrochemical sensing device according to claim 23 wherein the film thickness on the substrate is 10 to 200 nm.

25. An electrochemical sensing device according to claim 24, wherein the film thickness is 60 to 120 nm.

26. An electrochemical sensing device according to claim 21, wherein the electrode is made of materials selected from the group consisting of gold, silver, platinum, palladium, iridium, lead and alloys of those materials, carbon, carbon mixed with a binding material, and silver partially covered with a porous layer of an insoluble silver salt.

27. An electrochemical sensing device according to claim 26, wherein the insoluble silver salt is silver chloride, silver bromide, silver iodide, silver ferricyanide or silver ferrocyanide.

28. An electrochemical sensing device according to claim 21, wherein there are two or more electrodes and they are disposed on one side of the substrate or on opposite sides of the substrate.

29. An electrochemical sensing device according to claim 21, further including a blocker in the substrate which assists in preventing transport of material in the compressed region.

30. An electrochemical sensing device according to claim 29, wherein the blocker is glucose, agar, gelatine or starch.

31. An electrochemical sensing device according to claim 29, wherein the blocker is loaded into the precompressed porous substrate using the steps of:

a) dissolving the blocker in a suitable solvent;

b) wetting the substrate with the solution of the blocker; and then c) removing the solvent by evaporation.

32. An electrochemical sensing device according to claim 21, to wherein the substrate is made of a porous material selected from the group consisting of polymers or mixtures of polymers.

33. An electrochemical sensing device according to claim 32, wherein the polymers or mixtures of polymers consist of polysulfones, polyvinylidene halides, tetrafluoroethene, polyamides, polyimides, polyethylene, polypropylene, polyacrylonitrates or polycarbonates.

34. An electrochemical sensing device according to claim 33, wherein the polyvinylidene halides are polyvinylidene difluorides.

35. An electrochemical sensing device according to any claim 21, wherein the thickness of the precompressed substrate is about 180 μm or less.

36. An electrochemical sensing device according to claim 35, wherein the thickness of the precompressed substrate is from 30 μm to 150 μm.

37. An electrochemical sensing device according to claim 21, wherein the pore size of the substrate ranges from 10 kilodaltons cut-off (lower limit) to 5 microns.

38. An electrochemical sensing device according to claim 37, wherein the pore size of the substrate ranges from 0.1 μm to 0.8 μm.

39. An electrochemical sensing device according to claim 38, wherein the pore size of the substrate ranges from 0.2 μm to 0.5 μm.

40. An electrochemical sensing device according to claim 21, wherein the porous substrate is a membrane that is permeable to a fluid containing a first species to be analyzed but substantially impermeable to a second species contained in the fluid, the second species being of a kind which would interfere with the electrochemical sensing of the first species.

* * * * *